US012711594B2

(12) United States Patent
Varghese et al.

(10) Patent No.: US 12,711,594 B2
(45) Date of Patent: Aug. 18, 2026

(54) METHODS AND APPARATUS FOR ANALYSING IMAGES OF HAIR AND SKIN ON A BODY OF A SUBJECT

(71) Applicant: KONINKLIJKE PHILIPS N.V., Eindhoven (NL)

(72) Inventors: Babu Varghese, Eindhoven (NL); Jonathan Alambra Palero, Waalre (NL); Yannyk Parulian Julian Bourquin, Eindhoven (NL); Rieko Verhagen, Vught (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 230 days.

(21) Appl. No.: 18/698,814

(22) PCT Filed: Sep. 29, 2022

(86) PCT No.: PCT/EP2022/077110
§ 371 (c)(1),
(2) Date: Apr. 5, 2024

(87) PCT Pub. No.: WO2023/057299
PCT Pub. Date: Apr. 13, 2023

(65) Prior Publication Data

US 2025/0238910 A1 Jul. 24, 2025

(30) Foreign Application Priority Data

Oct. 7, 2021 (EP) ..................................... 21201516

(51) Int. Cl.

| | |
|---|---|
| ***G06T 7/00*** | (2017.01) |
| ***A61B 5/00*** | (2006.01) |
| ***G06T 7/90*** | (2017.01) |

(52) U.S. Cl.
CPC .............. *G06T 7/0002* (2013.01); *G06T 7/90* (2017.01); *A61B 5/441* (2013.01); *A61B 5/448* (2013.01);
(Continued)

(58) Field of Classification Search
CPC ....... A61B 5/441; A61B 5/448; A61B 5/0075; G06T 2207/30088; G06T 2207/10048;
(Continued)

(56) References Cited

U.S. PATENT DOCUMENTS

| | | | | |
|---|---|---|---|---|
| 11,631,164 B2 * | 4/2023 | McCall | .................. | H04N 23/55 348/135 |
| 2003/0053664 A1 * | 3/2003 | Pavlidis | ............... | G06V 40/161 382/117 |

(Continued)

FOREIGN PATENT DOCUMENTS

| | | |
|---|---|---|
| JP | 2007133560 A * | 5/2007 |
| JP | 4442472 B2 * | 3/2010 |

(Continued)

OTHER PUBLICATIONS

I. C. Setiadi and A. M. T. Nasution, “Design and characterization of a LED-based multispectral imaging system applied to dermatology,” 2018 International Conference on Signals and Systems (ICSigSys), Bali, Indonesia, 2018, pp. 229-235, doi: 10.1109/ICSIGSYS.2018.8372763 (Year: 2018).*

(Continued)

*Primary Examiner* — Michael Robert Cammarata

(57) ABSTRACT

According to an aspect, there is provided a computer-implemented method configured for analysing images of hair and skin on a body of a subject. The method comprises (i) receiving (101) one or more images of a body part of the subject, the one or more images comprising a skin region
(Continued)

corresponding to skin on the body part and a hair region corresponding to hair on the body part; (ii) processing (103) the one or more images to determine diffuse reflectance of the skin region at different wavelengths of light; (iii) processing (105) the one or more images to determine diffuse reflectance of the hair region at different wavelengths of light; (iv) determining (107) a first contrast measure for a first pair of values of first and second wavelengths, wherein the first contrast measure is determined from the diffuse reflectance intensities for the skin region and the hair region in first and second spectral bands of light, wherein the first and second spectral bands are respectively centred on the value of the first wavelength and the value of the second wavelength in the first pair of values; (v) repeating (109) step (iv) to determine one or more further contrast measures for respective further pairs of values of the first and second wavelengths; and (vi) selecting (111) first and second spectral bands corresponding to the pair of values of the first and second wavelengths that provides a contrast measure that meets a criterion; wherein each value of the first wavelength is in the range between 425 nm and 650 nm, and each value of the second wavelength is in the range between 600 nm and 850 nm, wherein in a pair of values, the value of the first wavelength is different to the value of the second wavelength.

14 Claims, 9 Drawing Sheets

(52) U.S. Cl.
CPC ............... *G06T 2207/10024* (2013.01); *G06T 2207/10152* (2013.01); *G06T 2207/30088* (2013.01)

(58) Field of Classification Search
CPC ... G06T 2207/20224; G06T 7/90; G06T 5/50; G06V 10/143
See application file for complete search history.

(56) References Cited

U.S. PATENT DOCUMENTS

2003/0169901 A1* 9/2003 Pavlidis ................. G06V 40/10 382/103
2006/0149151 A1 7/2006 Ladjevardi et al.
2012/0002204 A1* 1/2012 Varghese ............... G01N 21/23 356/369
2012/0224042 A1 9/2012 Saijo
2014/0012135 A1* 1/2014 Freeman ................ A61B 5/445 600/407
2016/0022181 A1* 1/2016 Valsan ................. A61B 5/0261 600/323
2016/0167241 A1 6/2016 Goldfarb et al.
2017/0079530 A1* 3/2017 DiMaio ................ A61B 5/0261
2018/0106676 A1* 4/2018 Jang ....................... A61B 5/441
2018/0137609 A1* 5/2018 Barker ...................... G06T 5/92
2019/0200871 A1* 7/2019 De Haan ............ A61B 5/14552
2019/0239752 A1 8/2019 Dumitrescu et al.
2020/0298016 A1* 9/2020 Yoon .................... A61N 5/0616
2020/0345293 A1* 11/2020 Ras ...................... A61B 5/0077
2020/0375466 A1* 12/2020 Ras ........................ A61B 5/443
2021/0067672 A1 3/2021 Binder
2021/0086379 A1 3/2021 Brette
2021/0166361 A1* 6/2021 Fukushi .................... G06T 5/50
2024/0048823 A1* 2/2024 Yu ............................. G01J 3/28

FOREIGN PATENT DOCUMENTS

JP 2017173764 A * 9/2017
WO 2019234144 A1 12/2019

OTHER PUBLICATIONS

Shahzad A, Saad MN, Walter N, Malik AS, Meriaudeau F. Hyperspectral venous image quality assessment for optimum illumination range selection based on skin tone characteristics. Biomed Eng Online. Aug. 3, 2014;13:109. doi: 10.1186/1475-925X-13-109. PMID: 25087016; PMCID: PMC4132203. (Year: 2014).*
Mark D. Shriver et al. "Comparison of Narrow-Bank Reflectance Spectroscopy and Tristimulus Colorimetry for Measurements of Skin and Hair Color in Persons of Different Biological Ancestry". American Journal of Physical Anthropology, vol. 112, No. 1, Apr. 13, 2000, pp. 17-27. (Year: 2000).*
D. D. Gomez, J. M. Carstensen and B. J. Ersbell, "Precise multi-spectral dermatological imaging," IEEE Symposium Conference Record Nuclear Science 2004., Rome, Italy, 2004, pp. 3262-3266 vol. 5, doi: 10.1109/NSSMIC.2004.1466382. keywords: (Year: 2004).*
Y. Yacoob and L. S. Davis, "Detection and analysis of hair," in IEEE Transactions on Pattern Analysis and Machine Intelligence, vol. 28, No. 7, pp. 1164-1169, Jul. 2006, doi: 10.1109/TPAMI.2006.139. (Year: 2006).*
Suzuki et al., "Detection of Skin Region from Multibrand Near-IR Spectral Characteristics", Electronics and Communications in Japan, vol. 92, No. 11, (2009).
International Search report and Written Opinion of PCT/EP2022/077110, dated Sep. 29, 2022.

* cited by examiner

METHODS AND APPARATUS FOR ANALYSING IMAGES OF HAIR AND SKIN ON A BODY OF A SUBJECT

CROSS-REFERENCE TO PRIOR APPLICATIONS

This application is the U.S. National Phase application under 35 U.S.C. § 371 of International Application No. PCT/EP2022/077110, filed on Sep. 29, 2022, which claims the benefit of European Patent Application No. 21201516.8, filed on Oct. 7, 2021. These applications are hereby incorporated by reference herein.

FIELD OF THE INVENTION

This disclosure relates to methods and apparatus for analysing images of hair and skin on a body of a subject.

BACKGROUND OF THE INVENTION

There are many different types of personal care operations in which images of hair and skin can be evaluated to determine properties of the skin, hair or both, with those properties being taken into account when performing the personal care operation, or when providing guidance or recommendations to a user of a personal care device that is to perform a personal care operation. Exemplary personal care operations include shaving, hair cutting, hair removal, hair regrowth, photoepilation, skin massage, skin light treatment, etc. In a hair cutting or shaving device, it can be useful, for example, to determine a thickness or density of hairs to be cut or shaved, as this can be used to adjust the cutting or shaving parameters of the personal care device. In a photoepilation or skin light treatment device, it can be useful, for example, to determine a thickness or colour of hairs, or a skin tone, in order to use an appropriate power and/or wavelength of light, and also useful to determine a hair count per area during the course of treatment to allow for the efficacy of the photoepilation treatment to be monitored.

While it is straightforward to obtain images of hair and skin, for example using a camera on a smartphone, tablet or smart mirror, etc., it is not always straightforward to analyse the images to distinguish between the hair and skin in the image or to determine properties of the hair and skin in the image. It is known that skin and hair properties vary from person to person, and so a common approach to define skin types and hair types and to derive suitable parameters from those general types to "optimise" hair recognition on skin. However, given the variation of skin types and hair types, and the combinations thereof, such optimisation is not in fact optimal.

FIG. 1 illustrates different skin type and hair colour combinations. Six skin types are defined, labelled I-VI, from lightest (type I) to darkest (type VI), and six hair colours, including grey, light blond, dark blond, light brown, dark brown and black. The grid 2 shows the possible combinations of skin type and hair colour, with six of those combinations (the ones marked with hatching) not being considered possible. The example images 4, 5, 6, 7 were obtained by a device using common settings of different skin type/hair colour combinations. Image 4 is for a subject with a dark skin type and black hair, image 5 is for a subject with a light skin type and black hair, image 6 is for a subject with a light skin type and brown hair, and image 7 is for a subject with a light skin type and grey/blond hair. In images 4, 5 and 6 the hairs are readily distinguishable, whereas in image 7 the hairs are difficult to see due to a poor optical hair-skin contrast.

It is noted that US 2012/0224042 A1 discloses a method which might detect a skin region by having two LEDs emitting light at different wavelengths, a camera receiving reflected light from an object at different timings creating first and second up images which include at least a skin detection region used for detecting the skin region.

It is further noted that in the paper titled "Detection of Skin Region from Multiband Near-IR Spectral Characteristics", published in Electronics and Communicalions in Japan, Vol. 92, No. 11, 2009, it is discussed that a drivers face region can be detected by a camera during nighttime driving by using unique reflecting characteristics of materials.

SUMMARY OF THE INVENTION

In the case of shaving, simulations and user test results show that taking into account user characteristics and variation (e.g. hair, skin, user handling) can be more important for the end shaving performance results than further general improvements that could be made to the mechanical design of the shaver. Objective and subjective test results support this, showing a much larger spread between users than between types of shavers.

Thus, shaving performance can be improved by taking into account individual differences in hair and/or skin type, and similar benefits are expected for other types of personal care operations too. A user's hair and/or skin type, and hair and skin properties relevant for the personal care operation, can be determined using a sensor or a questionnaire. The properties of hairs which can be relevant for personalisation of a personal care operation, can include colour, thickness, shape, density and/or orientation. The properties of skin which can be relevant for personalisation of a personal care operation, can include colour, tone, the presence of scars, moles, freckles, spots, etc.

The optical properties of skin and hair are similar and therefore the contrast between the two is limited. This contrast is dependent not only on the colour of the skin and hair but also on other properties of the skin and hair. For instance, an optical method that provides a high contrast with respect to the colour of skin and hair, can mean that light and thin hairs (e.g. non-medullated blond hairs) on light skin (i.e. skin type 1-2)—such as in image 10—would be hard to detect. This can lead to poor efficacy for hair detection and thus may deteriorate the possibilities for personalisation.

Therefore, there is a need for improvements in the analysis of images of hair and skin on a body of a subject, and in particular to a technique for selecting spectral bands for a subject that enables or improves the analysis of an image of the subject's skin and hair.

According to a first specific aspect, there is provided a computer-implemented method configured for analysing images of hair and skin on a body of a subject. The method comprises (i) receiving one or more images of a body part of the subject, the one or more images comprising a skin region corresponding to skin on the body part and a hair region corresponding to hair on the body part; (ii) processing the one or more images to determine diffuse reflectance of the skin region at different wavelengths of light; (iii) processing the one or more images to determine diffuse reflectance of the hair region at different wavelengths of light; (iv) determining a first contrast measure for a first pair of values of first and second wavelengths, wherein the first contrast measure is determined from the diffuse reflectance intensities for the skin region and the hair region in first and second spectral bands of light, wherein the first and second spectral bands are respectively centred on the value of the first wavelength and the value of the second wavelength in the first pair of values; (v) repeating step (iv) to determine one or more further contrast measures for respective further pairs of values of the first and second wavelengths; and (vi) selecting first and second spectral bands corresponding to the pair of values of the first and second wavelengths that provides a contrast measure that meets a criterion; wherein each value of the first wavelength is in the range between 425 nm and 650 nm, and each value of the second wavelength is in the range between 600 nm and 850 nm, wherein in a pair of values, the value of the first wavelength is different to the value of the second wavelength. Thus, the first aspect provides a technique for selecting spectral bands for a subject that enables or improves the analysis of an image of the subject's skin and hair.

Step (iv) comprises determining the first contrast measure from (a) a difference between the diffuse reflectance intensity for the skin region in the first spectral band and the diffuse reflectance intensity for the skin region in the second spectral band, and (b) a difference between the diffuse reflectance intensity for the hair region in the first spectral band and the diffuse reflectance intensity for the hair region in the second spectral band. In these embodiments, step (iv) can comprise determining the first contrast measure as a ratio of the differences.

In some embodiments, one of: the criterion is met if the magnitude of the contrast measure is above a threshold; the criterion is met if the magnitude of the contrast measure is below a threshold; the criterion is met if the contrast measure is the highest of the determined contrast measures; the criterion is met if the contrast measure is the lowest of the determined contrast measures; and the criterion is met if the contrast measure is an optimal value.

In some embodiments, the method further comprises controlling one or more light sources to concurrently or separately illuminate the subject with light including wavelengths corresponding to the selected first and second spectral bands; and receiving one or more further images of the subject while the subject is illuminated with the light including wavelengths corresponding to the selected first and second spectral bands. In these embodiments, the method can further comprise analysing the received one or more further images to determine one or more properties of the skin and/or hair of the subject.

In alternative embodiments, the method further comprises analysing the received one or more images in the selected first and second spectral bands to determine one or more properties of the skin and/or hair of the subject.

In some embodiments, the method further comprises receiving or determining an indication of the skin tone of the subject and/or the hair colour of the subject in the received one or more images. In these embodiments, the method can further comprise repeating the method on images of hair and skin for a plurality of different subjects having different skin tones and/or different hair colours. In these embodiments, the method can further comprise: storing, in a look-up table or database, an indication of the selected first and second spectral bands, and/or an indication of the pair of values of the first and second wavelengths corresponding to the selected first and second spectral bands, and the corresponding indication of the tone of the skin and/or colour of the hair. In these embodiments, the method can further comprise: receiving an indication of a skin tone and/or a hair colour of a further subject to be imaged; and using the look-up table or database to determine first and second spectral bands to use for imaging the further subject according to the skin tone and/or hair colour in the received indication. In these embodiments, the method can further comprise: controlling one or more light sources to illuminate the further subject with light including wavelengths corresponding to the determined first and second spectral bands; and obtaining an image of the further subject while the subject is illuminated with the light including wavelengths corresponding to the determined first and second spectral bands. In these embodiments, the method can further comprise analysing the obtained image of the further subject in the determined first and second spectral bands to determine one or more properties of the skin and/or hair of the further subject.

According to a second aspect, there is provided a computer program product comprising a computer readable medium having computer readable code embodied therein, the computer readable code being configured such that, on execution by a suitable computer or processor, the computer or processor is caused to perform the method according to the first aspect or any embodiment thereof.

According to a third aspect, there is provided an apparatus configured for analysing images of hair and skin on a body of a subject. The apparatus is configured to: (i) receive one or more images of a body part of the subject, the image comprising a skin region corresponding to skin on the body part and a hair region corresponding to hair on the body part; (ii) process the one or more images to determine diffuse reflectance of the skin region at different wavelengths of light; (iii) process the one or more images to determine diffuse reflectance of the hair region at different wavelengths of light; (iv) determine a first contrast measure for a first pair of values of first and second wavelengths, wherein the first contrast measure is determined from the diffuse reflectance intensities for the skin region and the hair region in first and second spectral bands of light, wherein the first and second spectral bands are respectively centred on the value of the first wavelength and the value of the second wavelength in the first pair of values; (v) repeat operation (iv) to determine one or more further contrast measures for respective further pairs of values of the first and second wavelengths; and (vi) select first and second spectral bands corresponding to the pair of values of the first and second wavelengths that provides a contrast measure that meets a criterion; wherein each value of the first wavelength is in the range between 425 nm and 650 nm, and each value of the second wavelength is in the range between 600 nm and 850 nm, wherein in a pair of values, the value of the first wavelength is different to the value of the second wavelength.

In some embodiments, the apparatus is configured to receive the one or more images from an image acquisition unit or a memory unit. In some embodiments, the image acquisition unit comprises an illumination unit for generating light to illuminate the subject when an image is to be acquired. In some embodiments, the illumination unit is configured to selectively generate light in specific spectral bands.

In some embodiments, the apparatus further comprises the image acquisition unit. In other embodiments, the apparatus is part of a system that comprises the image acquisition unit. Further embodiments of the third aspect are also provided in which the apparatus is further configured to perform the method according to any of the various embodiments of the first aspect.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF THE EMBODIMENTS

As noted above, it can be useful to be able to analyse images of skin and hair of a subject, for example to enable parameters of a personal care operation to be adapted to the subject. As outlined below, it has been found that using particular wavelengths of light to obtain images from a subject can improve the contrast between the hair and skin in the image, enabling properties of the hair and/or skin to be more easily derived. Due to the different optical properties of different skin types and hair colours, there is no universal set of wavelengths that are applicable to all subjects, and so the techniques described herein provide a technique for selecting spectral bands centred on specific wavelengths for a subject that enables or improves the analysis of an image of the subject's skin and hair, in particular, facial hair.

Before describing the technique and apparatus for implementing the technique in more detail, a discussion of the principles underlying the technique is provided.

Figure 1:
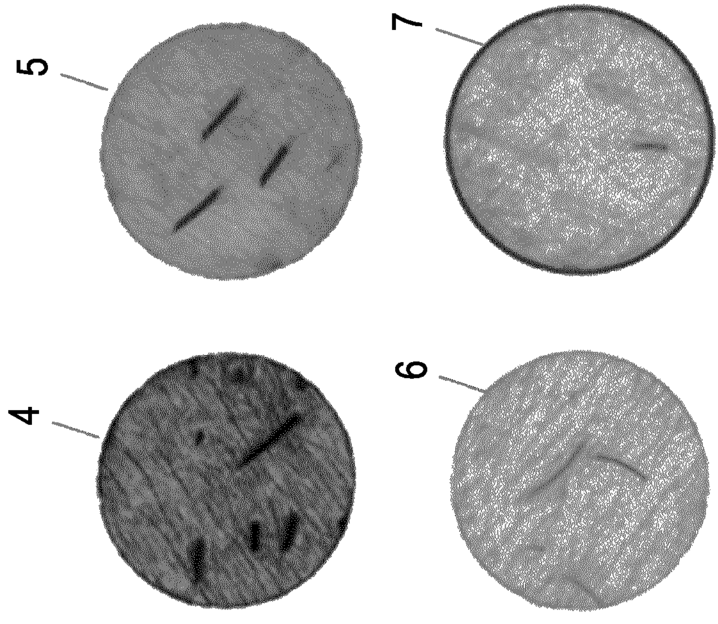
FIG. 1 illustrates combinations of skin types and hair colour and shows some example images.
Figure 1:
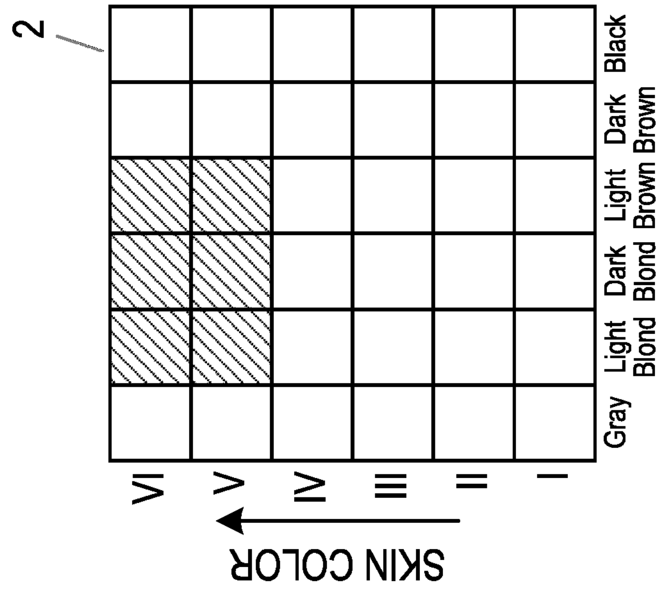
Figure 2:
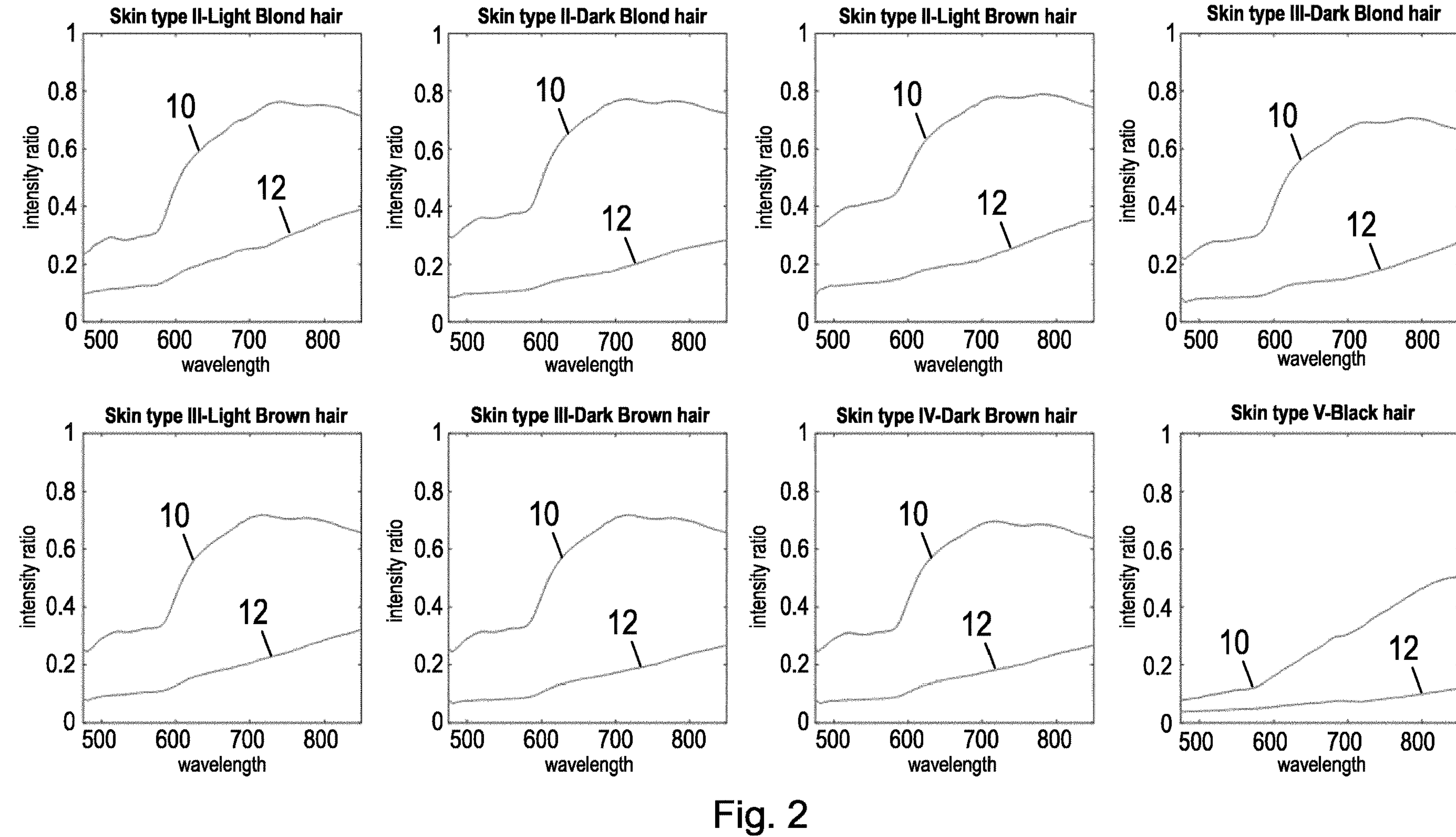
FIG. 2 is a set of graphs illustrating diffuse reflectance spectra for skin and hair for a number of subjects with different skin types and hair colours.

In the following, the preliminary results obtained using a hyperspectral imaging system are discussed. An aim of this pilot experiment was to identify a spectral band which shows a maximum hair-skin contrast for all hair-skin types (i.e. all combinations of hair colour and skin type). Hyperspectral imaging of the full face of several subjects was performed using a hyperspectral imaging set-up that utilises polarised white light illumination and cross-polarised detection of the light reflected from the skin in a bandwidth of 420 nanometres (nm)-1100 nm in steps of 5 nm. Experiments were performed on eight test subjects with different skin types, and the results are shown in FIG. 2. It should be noted that the hyperspectral imaging set-up is not required for implementing the techniques described herein, and thus further details are not provided.

FIG. 2 shows a graph for each subject, showing the ratio of light intensity detected from the skin for different wavelengths (shown by line 10) and the ratio of light intensity from hairs for different wavelengths (shown by line 12). The ratio of light intensity across the range of wavelengths detected from the skin is referred to herein as a "skin diffuse reflectance spectrum" and the ratio of light intensity across the range of wavelengths detected from the hair is referred to herein as a "hair diffuse reflectance spectrum". The eight subjects have different combinations of skin type and hair colour. From left to right in the top row of graphs, the subjects have skin type II and light blond hair, skin type II and dark blond hair, skin type II and light brown hair, and skin type III and dark blond hair. From left to right in the bottom row of graphs, the subjects have skin type III and light brown hair, skin type III and dark brown hair, skin type IV and dark brown hair, and skin type V and black hair.

It can also be seen from FIG. 2 that the hair-skin contrast is a maximum around in a spectral band between 550 nm and 850 nm, but the optimal range and position of the band depends on the specific hair-skin type for the subject.

In view of these results, a difference imaging technique is proposed in which light in two or more particular spectral bands reflected from the skin and hair is evaluated in order to enhance the contrast between the skin and hair. The centre wavelength of each spectral band will depend on the subject (and in particular their skin type and/or hair colour), and in some embodiments the width of the spectral band also depends on the subject (and in particular their skin type and/or hair colour). In the following, the techniques are described with reference to the use of light in two spectral bands, but it will be appreciated that the techniques can use light in three or more spectral bands. Table 1 below sets out the broad wavelength bands within which the centre wavelengths of two particular spectral bands for any subject will reside. The spectral bands are defined by respective centre wavelengths, denoted $\lambda_1$ and $\lambda_2$ respectively. Table 1 shows that, regardless of the skin type and hair colour, the first spectral band has its centre wavelength $\lambda_1$ in the range between 600 nm and 850 nm, and the second spectral band has its centre wavelength $\lambda_2$ in the range between 425 nm and 650 nm.

TABLE 1

| Skin type/Hair color | $\lambda_2$(nm) center | $\lambda_1$(nm) center |
|---|---|---|
| Skin type II: | | |
| Light Blond hair | 425-650 nm | 600-850 nm |
| Dark Blond hair | 425-640 nm | 640-850 nm |
| Light Brown hair | 425-630 nm | 630-850 nm |
| Skin type III: | | |
| Dark Blond hair | 425-650 nm | 615-850 nm |
| Light Brown hair | 425-650 nm | 605-850 nm |
| Dark Brown hair | 425-650 nm | 600-850 nm |
| Skin type IV: | | |
| Dark Brown hair | 425-650 nm | 600-850 nm |
| Skin type V: | | |
| Black hair | 425-600 nm | 650-850 nm |

Tables 2-9 below show the contrast obtained for different pairs of spectral band centre wavelengths, with the contrast being derived from the diffuse reflectance spectra shown in FIG. 2. Thus, Table 2 shows the contrast obtained for different combinations of first and second spectral bands for a subject with skin type II and light blond hair.

TABLE 2

| $\lambda_2$ (nm) | $\lambda_1$ (nm) | CONTRAST ($\times 10^3$) |
|---|---|---|
| 499 | 651 | 1.0 |
| 525 | 675 | 1.3 |
| 539 | 689 | 1.1 |
| 547 | 701 | 3.9 |
| 555 | 715 | 1.7 |
| 571 | 739 | 1.9 |
| 581 | 753 | 1.3 |
| 605 | 793 | 1.7 |
| 615 | 813 | 9.6 |
| 619 | 823 | 4.5 |
| 641 | 825 | 0.1 |

Table 3 shows the contrast obtained for different combinations of first and second spectral bands for a subject with skin type II and dark blond hair.

TABLE 3

| $\lambda_2$ (nm) | $\lambda_1$ (nm) | CONTRAST ($\times 10^3$) |
|---|---|---|
| 475 | 665 | 0.7 |
| 485 | 681 | 1.5 |
| 497 | 699 | 0.9 |
| 507 | 711 | 0.8 |
| 531 | 733 | 1.7 |
| 575 | 769 | 19.9 |
| 583 | 779 | 4.7 |
| 595 | 797 | 5.1 |
| 607 | 819 | 0.9 |
| 609 | 823 | 0.7 |

Table 4 shows the contrast obtained for different combinations of first and second spectral bands for a subject with skin type II and light brown hair.

TABLE 4

| $\lambda_2$ (nm) | $\lambda_1$ (nm) | CONTRAST ($\times 10^3$) |
|---|---|---|
| 475 | 655 | 0.4 |
| 483 | 677 | 2.2 |
| 489 | 691 | 0.9 |
| 491 | 695 | 0.5 |
| 547 | 761 | 0.3 |
| 555 | 767 | 0.5 |
| 569 | 779 | 2.3 |
| 585 | 797 | 2.2 |
| 593 | 807 | 1.2 |
| 605 | 823 | 0.7 |

Table 5 shows the contrast obtained for different combinations of first and second spectral bands for a subject with skin type III and dark blond hair.

TABLE 5

| $\lambda_2$ (nm) | $\lambda_1$ (nm) | CONTRAST ($\times 10^3$) |
|---|---|---|
| 470 | 640 | 3.06 |
| 480 | 650 | 8.14 |
| 490 | 670 | 3.15 |
| 500 | 690 | 2.73 |
| 530 | 730 | 1.17 |
| 560 | 750 | 1.78 |
| 590 | 780 | 3.49 |
| 600 | 800 | 1.2 |
| 610 | 810 | 1.71 |
| 630 | 830 | 1.47 |

Table 6 shows the contrast obtained for different combinations of first and second spectral bands for a subject with skin type III and light brown hair.

TABLE 6

| $\lambda_2$ (nm) | $\lambda_1$ (nm) | CONTRAST ($\times 10^3$) |
|---|---|---|
| 475 | 615 | 0.3 |
| 493 | 633 | 38.7 |
| 519 | 675 | 9.6 |
| 539 | 697 | 9.0 |
| 581 | 753 | 34.6 |
| 591 | 769 | 24.4 |
| 603 | 789 | 19.6 |
| 611 | 803 | 5.0 |
| 615 | 813 | 6.3 |
| 621 | 825 | 114.0 |

Table 7 shows the contrast obtained for different combinations of first and second spectral bands for a subject with skin type III and dark brown hair.

TABLE 7

| $\lambda_2$ (nm) | $\lambda_1$ (nm) | CONTRAST ($\times 10^3$) |
|---|---|---|
| 470 | 630 | 1.89 |
| 480 | 630 | 1.44 |
| 510 | 660 | 1.25 |
| 520 | 670 | 1.1 |
| 530 | 690 | 0.88 |
| 570 | 740 | 1.55 |
| 590 | 760 | 7.83 |
| 600 | 790 | 0.69 |
| 610 | 810 | 1.06 |
| 620 | 810 | 5.03 |

Table 8 shows the contrast obtained for different combinations of first and second spectral bands for a subject with skin type IV and dark brown hair.

TABLE 8

| $\lambda_2$ (nm) | $\lambda_1$ (nm) | CONTRAST ($\times 10^3$) |
|---|---|---|
| 475 | 625 | 2.0 |
| 483 | 631 | 1.6 |
| 507 | 657 | 1.5 |
| 515 | 667 | 1.3 |
| 535 | 685 | 0.8 |
| 575 | 737 | 1.5 |
| 585 | 755 | 7.7 |
| 593 | 769 | 1.6 |
| 615 | 811 | 5.0 |
| 621 | 825 | 3.7 |

Table 9 shows the contrast obtained for different combinations of first and second spectral bands for a subject with skin type V and black hair.

TABLE 9

| $\lambda_2$ (nm) | $\lambda_1$ (nm) | CONTRAST ($\times 10^3$) |
|---|---|---|
| 477 | 687 | 10.7 |
| 491 | 731 | 10.6 |
| 507 | 751 | 27.4 |
| 545 | 783 | 10.9 |
| 579 | 815 | 5.4 |
| 581 | 817 | 10.5 |
| 583 | 819 | 20.6 |
| 585 | 821 | 66.4 |
| 587 | 823 | 27.8 |
| 589 | 825 | 11.3 |

Figure 3:
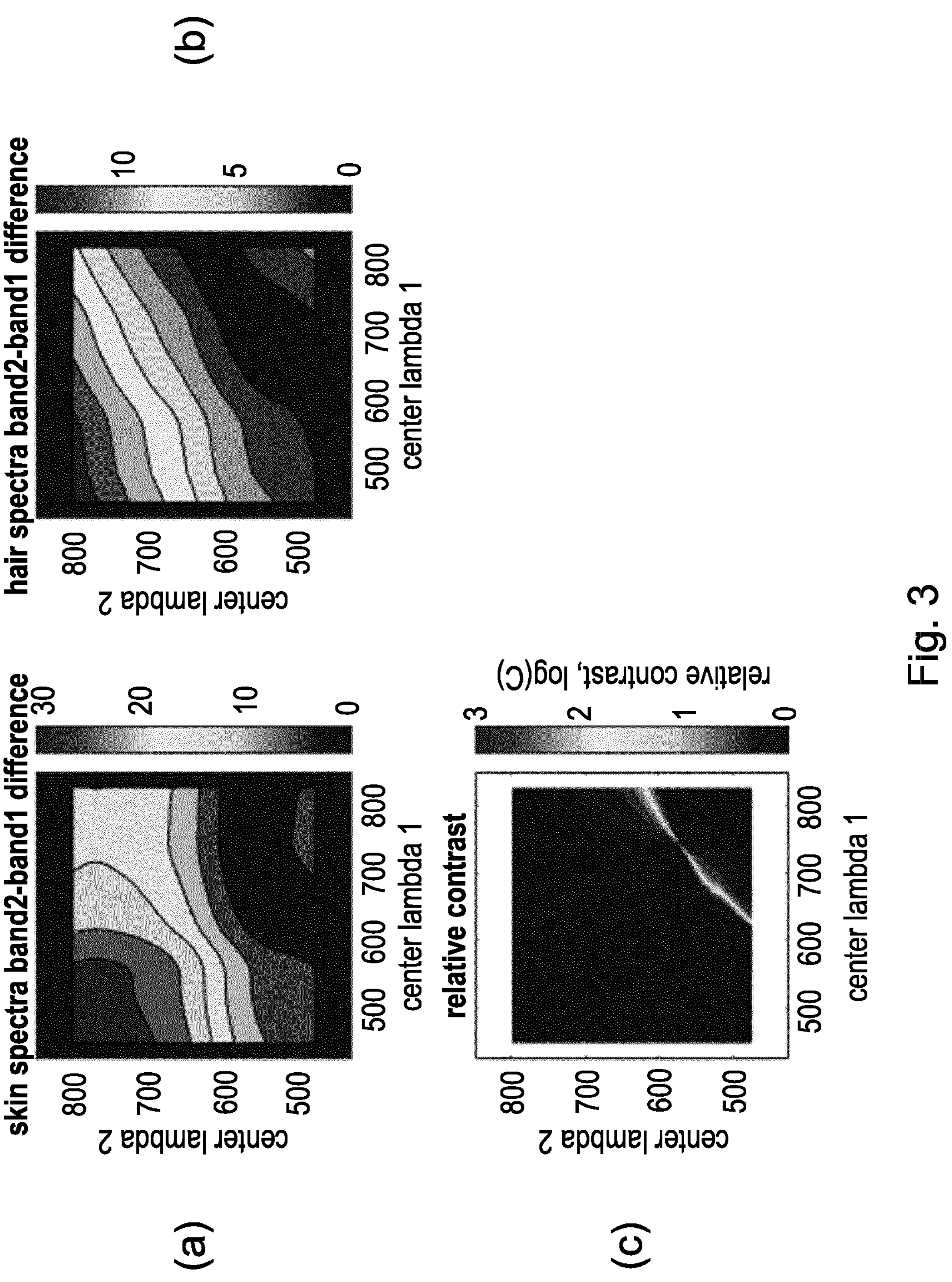
FIG. 3 shows dual spectral band differential matrices for a particular subject with skin type II and light blond hair.

FIG. 3 shows dual spectral band differential matrices for a particular subject with skin type II and light blond hair. The graph in FIG. 3(*a*) shows the spectral integrated intensity difference calculated between different pairs of spectral bands for skin, the graph shown in FIG. 3(*b*) shows the spectral integrated intensity difference calculated between different pairs of spectral bands for hair, and the graph in FIG. 3(*c*) shows the relative contrast in the form of a contour plot of the skin-to-hair dual spectral band differential contrast ratio. FIG. 3(*c*) allows for a visual determination of optimal wavelength pairs that result in high contrast between hair and skin. The relative contrast in FIG. 3(*c*) is derived as the ratio of the graph in FIG. 3(*a*) to the graph in FIG. 3(*b*).

Figure 4:
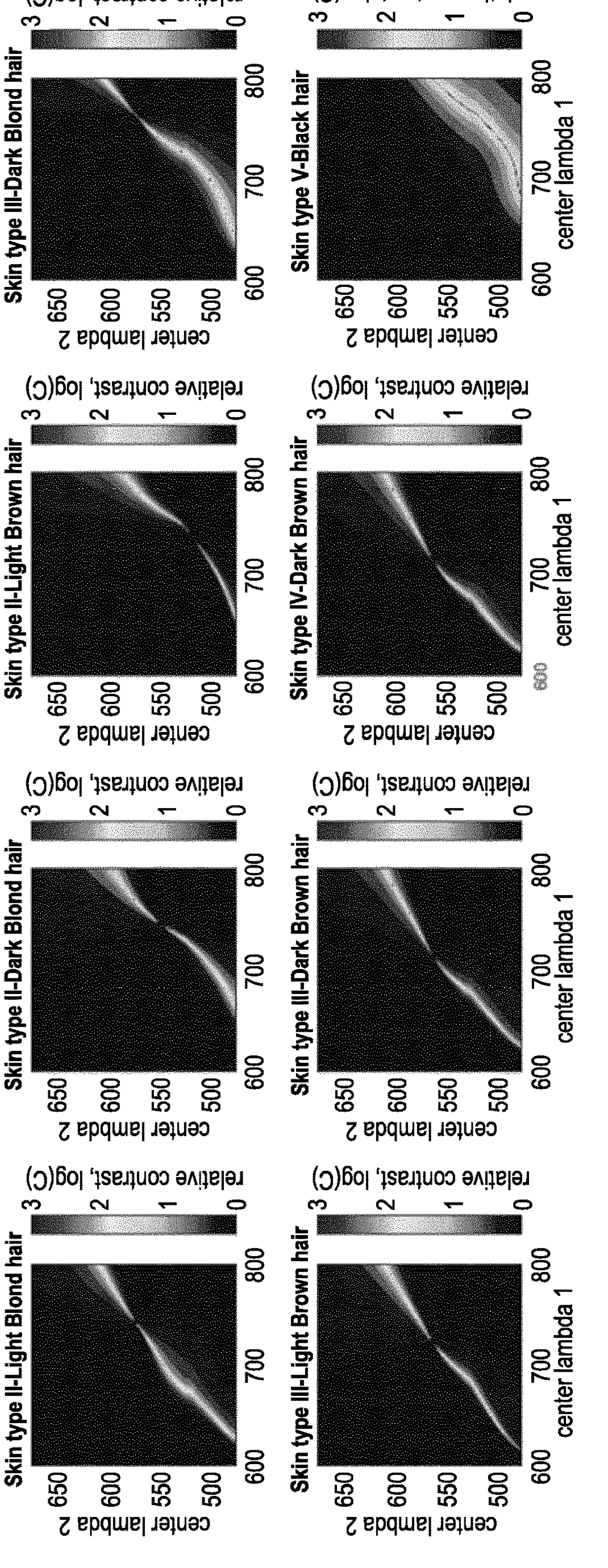
FIG. 4 shows graphs of the contrast ratio for different spectral bands for the eight subjects in FIG. 2.

FIG. 4 shows graphs of the contrast ratio-derived as shown in FIG. 3—for the eight subjects from FIG. 2. FIG. 4 shows that, for different skin and hair colour combinations, different optimal wavelength pairs result in maximum contrast values, and thus there is no wavelength pair that is applicable to all skin and hair colour combinations. Therefore, as provided by the techniques described herein, the wavelengths in the wavelength pair is 'tuned' for improved or maximum contrast for a specific hair-skin combination.

Figure 5:
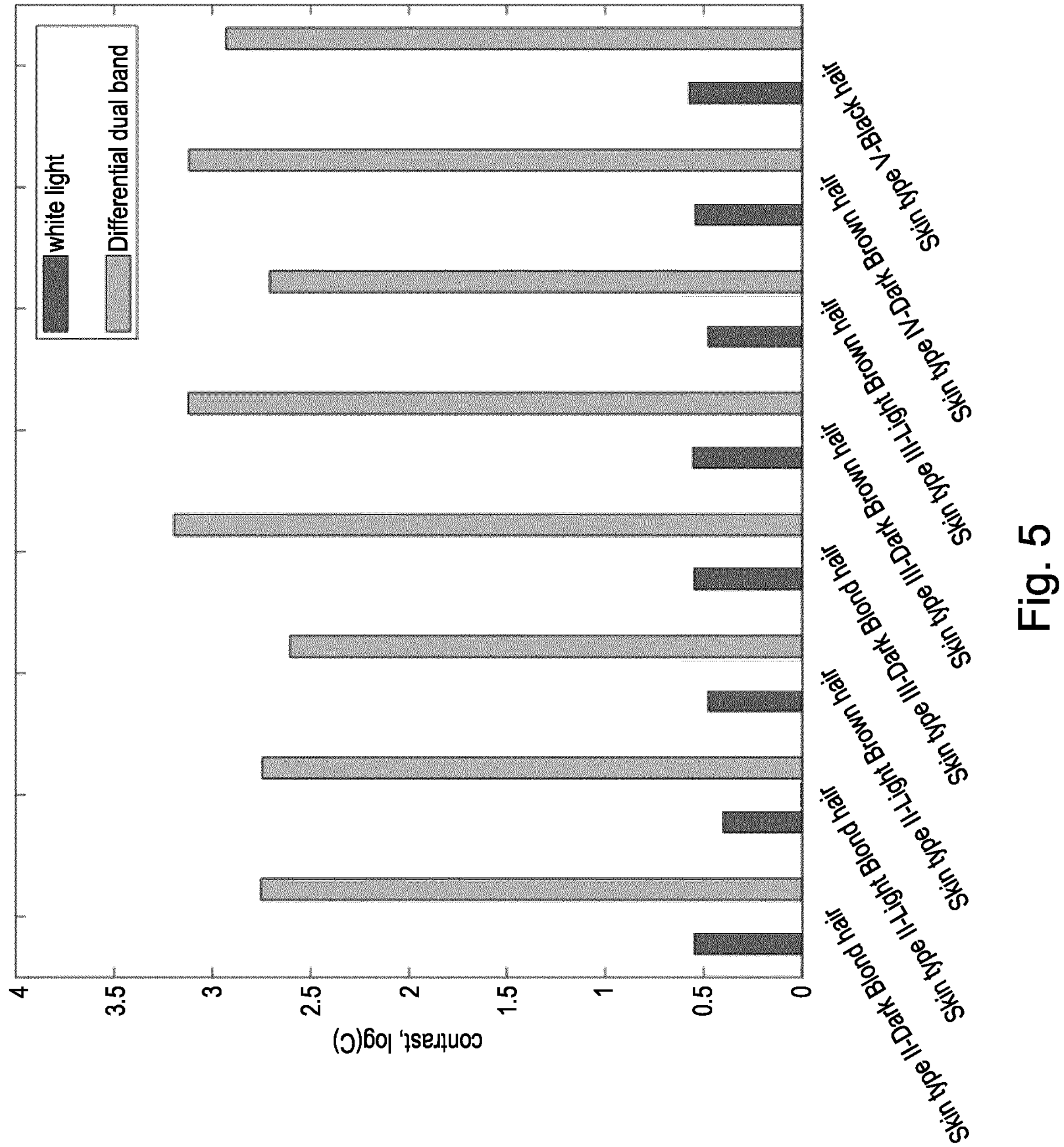
FIG. 5 is a graph illustrating the improvement in contrast between hair and skin in images obtained using the described techniques compared to images obtained using white light.

The graph in FIG. 5 illustrates the improvement in contrast between hair and skin in images obtained using the described techniques with suitable dual spectral bands for the eight subjects in FIGS. 2 and 4 compared to images obtained using white light.

Figure 6:
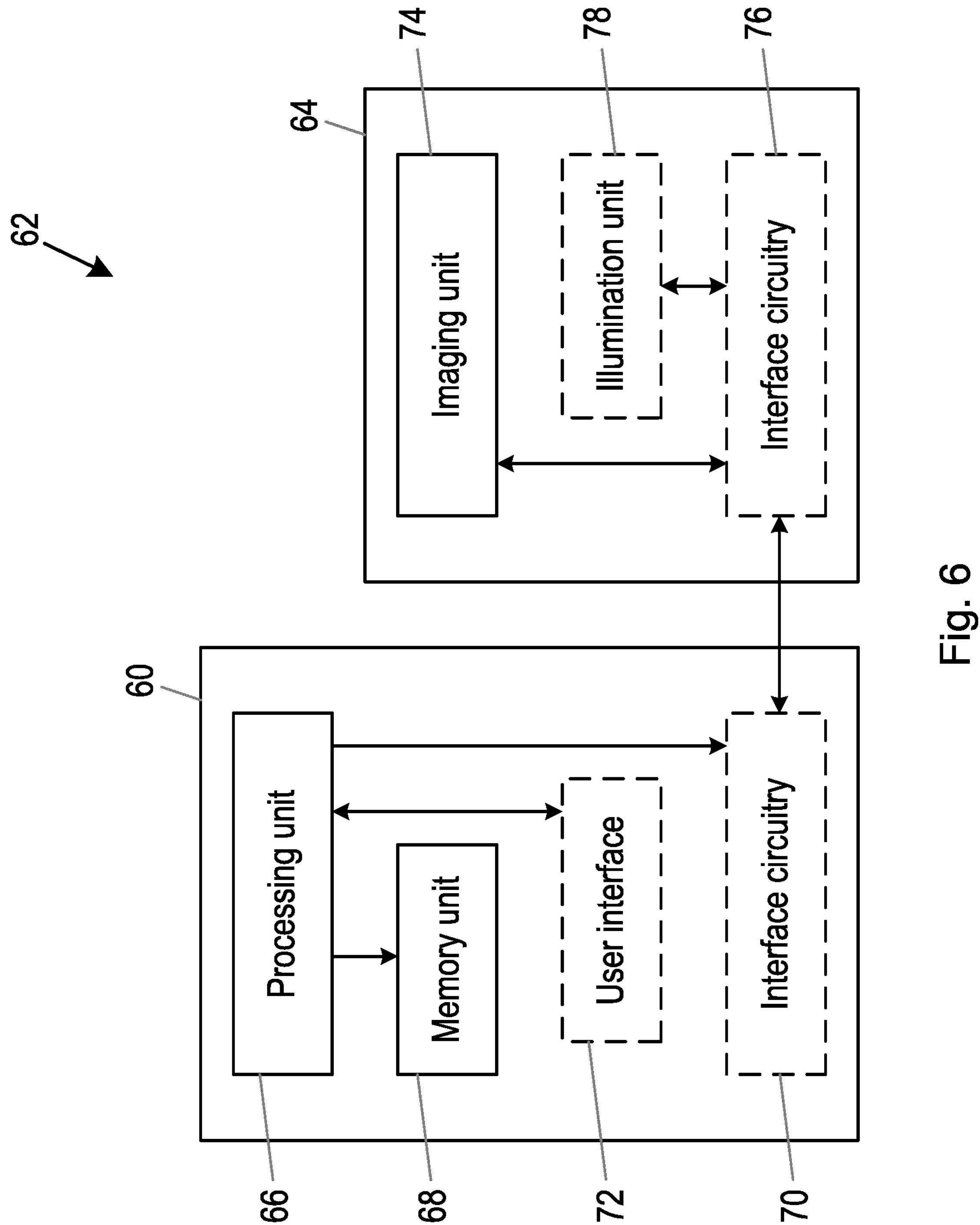
FIG. 6 illustrates an embodiment of an apparatus for analysing images of hair and skin on a body of a subject according to the techniques described herein.

The block diagram in FIG. 6 illustrates an embodiment of an apparatus 60 for analysing images of hair and skin on a body of a subject according to the techniques described herein. In this illustration, the apparatus 60 is shown as part of a system 62 that also includes a separate image acquisition unit 64 for obtaining one or more images of a subject. In alternative embodiments, the apparatus 60 can include the image acquisition unit 64, or otherwise include functionality for performing the functions of the image acquisition unit 64. In other embodiments the apparatus 60 can be implemented independently of any device or unit that obtains the images of the subject.

The apparatus 60 can be any type of electronic device or computing device. For example, the apparatus 60 can be, or be part of, a smartphone, a tablet, a smart watch, a smart mirror, a laptop, a computer or a server, for example a server in a data centre (also referred to as being 'in the cloud'). In some embodiments, the apparatus 60 can be, or be part of, a personal care device, for example a shaver, epilator, or skin treatment device. Where present, the image acquisition unit 64 may be in the form of, or be part of, a smartphone, a tablet, a smart watch, a smart mirror, a laptop, or other device capable of obtaining an image of a subject. In some embodiments, the image acquisition unit 64 may be in the form of, or be part of, a personal care device, for example a shaver, epilator, or skin treatment device.

The apparatus 60 includes a processing unit 66 that controls the operation of the apparatus 60 and that can be configured to execute or perform the methods described herein. The processing unit 66 can be implemented in numerous ways, with software and/or hardware, to perform the various functions described herein. The processing unit 66 may comprise one or more microprocessors or digital signal processors (DSPs) that may be programmed using software or computer program code to perform the required functions and/or to control components of the processing unit 66 to effect the required functions. The processing unit 66 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The processing unit 66 is connected to a memory unit 68 that can store data, information and/or signals for use by the processing unit 66 in controlling the operation of the apparatus 60 and/or in executing or performing the methods described herein. In some implementations the memory unit 68 stores computer-readable code that can be executed by the processing unit 66 so that the processing unit 66 performs one or more functions, including the methods described herein. The memory unit 68 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit 68 can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In some embodiments, the apparatus 60 can also comprise interface circuitry 70 for enabling a data connection to and/or data exchange with other devices, including, for example, image acquisition unit 64, and optionally any other devices such as servers, databases, user devices, etc. The connection may be direct or indirect (e.g. via the Internet), and thus the interface circuitry 70 can enable a connection between the apparatus 60 and image acquisition unit 64 via a network (such as the Internet), or directly between the apparatus 60 and image acquisition unit 64, via any desirable wired or wireless communication protocol. For example, the interface circuitry 70 can operate using WiFi, Bluetooth, Zigbee, or any cellular communication protocol. In the case of a wireless connection, the interface circuitry 70 (and thus apparatus 60) may include one or more suitable antennas for transmitting/receiving over a transmission medium (e.g. the air). Alternatively, in the case of a wireless connection, the interface circuitry 70 may include means (e.g. a connector or plug) to enable the interface circuitry 70 to be connected to one or more suitable antennas external to the apparatus 60 for transmitting/receiving over a transmission medium (e.g. the air). The interface circuitry 70 is connected to the processing unit 66 to enable information or data received by the interface circuitry 70 to be provided to the processing unit 66, and/or information or data from the processing unit 66 to be transmitted by the interface circuitry 70.

In some embodiments, the apparatus 60 comprises a user interface 72 that includes one or more components that enables a user of apparatus 60 (e.g. the subject) to input information, data and/or commands into the apparatus 60, and/or enables the apparatus 60 to output information or data to the user of the apparatus 60. For example the user interface 72 can include a display screen for displaying one or more images of the subject, and/or the results of analysis of images of the skin and hair of the subject. The user interface 72 can comprise any suitable input component(s), including but not limited to a keyboard, keypad, one or more buttons, switches or dials, a mouse, a track pad, a touch-screen, a stylus, a camera, a microphone, etc., and/or the user interface 72 can comprise any suitable output component(s), including but not limited to a display screen, one or more lights or light elements, one or more loudspeakers, a vibrating element, etc.

It will be appreciated that a practical implementation of apparatus 60 may include additional components to those shown in FIG. 6. For example, the apparatus 60 may also include a power supply, such as a battery, or components for enabling the apparatus 60 to be connected to a mains power supply.

The image acquisition unit 64 is provided to obtain one or more images of the skin and hair of the subject. These images are to be analysed by the apparatus 60 according to the techniques described herein, thus, the image acquisition unit 64 comprises an imaging unit 74 for obtaining images. The imaging unit 74 may include any suitable components for capturing one or more images or a video sequence comprising multiple images, for example a charge-coupled device (CCD) and one or more lenses and/or mirrors. In some embodiments, the imaging unit 74 is a camera, such as a digital camera. In some embodiments, the imaging unit 74 can be configured, or be configurable to, obtain images in one or more specific spectral bands, for example in at least two spectral bands with respective centre wavelengths in the range from 425 nm to 850 nm. For example, the imaging unit 74 may comprise one or more filters to enable light in the desired spectral band to be used to form the image. Alternatively, the sensor in the imaging unit 74 may be configured to only sense light in one or more specific spectral bands. In other embodiments the imaging unit 74 can be sensitive to light across the range from 425 nm to 850 nm, and subsequent processing of the image data can extract or select image data corresponding to a required spectral band.

In some embodiments, the image acquisition unit 64 can comprise interface circuitry 76 for enabling a data connection to and/or data exchange with other devices, including, for example, apparatus 60 (via interface circuitry 70), and optionally any other devices such as servers, databases, user devices, etc. The interface circuitry 76 can be implemented in a similar way to the interface circuitry 70 described above.

In some embodiments, the imaging unit 74 obtains images of the subject using the ambient light in the environment of the subject. However, in other embodiments the image acquisition unit 64 comprises an illumination unit 78 for generating light to illuminate the subject when an image is to be acquired by the imaging unit 74. The illumination unit 78 may be configured to generate white light or otherwise light across a broad spectrum of wavelengths, e.g. at least from 425 nm to 850 nm. In other embodiments the illumination unit 78 may be configured to selectively generate light in specific spectral bands, for example in at least two spectral bands with respective centre wavelengths in the range from 425 nm to 850 nm. The illumination unit 78 may be configured to generate the light in the specific spectral bands at the same time, or at different times (i.e. the illumination unit 78 can generate light in the first spectral band for a first time period and light in the second spectral band for a second time period). In some embodiments the illumination unit 78 is controllable to generate light in a required spectral band. In particular, the illumination unit 78 can be controlled to generate light in the two spectral bands identified according to the techniques described herein that are particularly suitable for the subject being imaged. In embodiments where the illumination unit 78 is to generate light in multiple spectral bands, the illumination unit 78 can be provided with a suitable arrangement of light sources, filters, etc. to enable light of the required wavelengths to be generated.

Figure 7:
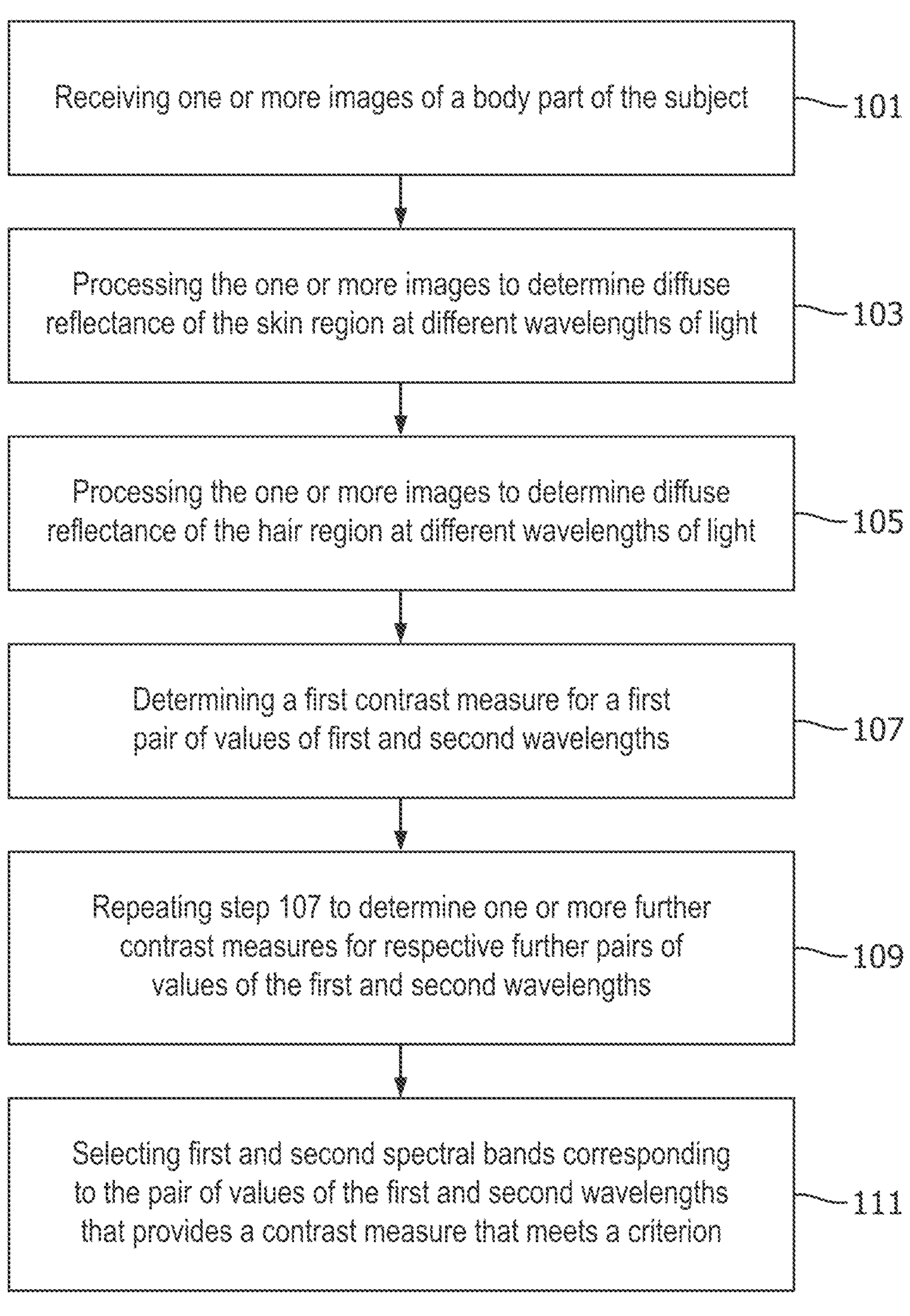
FIG. 7 is a flow chart illustrating a method of analysing images of hair and skin on a body of a subject.

The flow chart in FIG. 7 illustrates a method of analysing images of hair and skin on a body of a subject. The method can be implemented by the apparatus 60, for example by the processing unit 66 executing suitable computer code stored in the memory unit 68. The method is also described with reference to FIG. 8, which shows an exemplary image 80 and several graphs/plots 82-96 illustrating steps of the method.

Figure 8A:
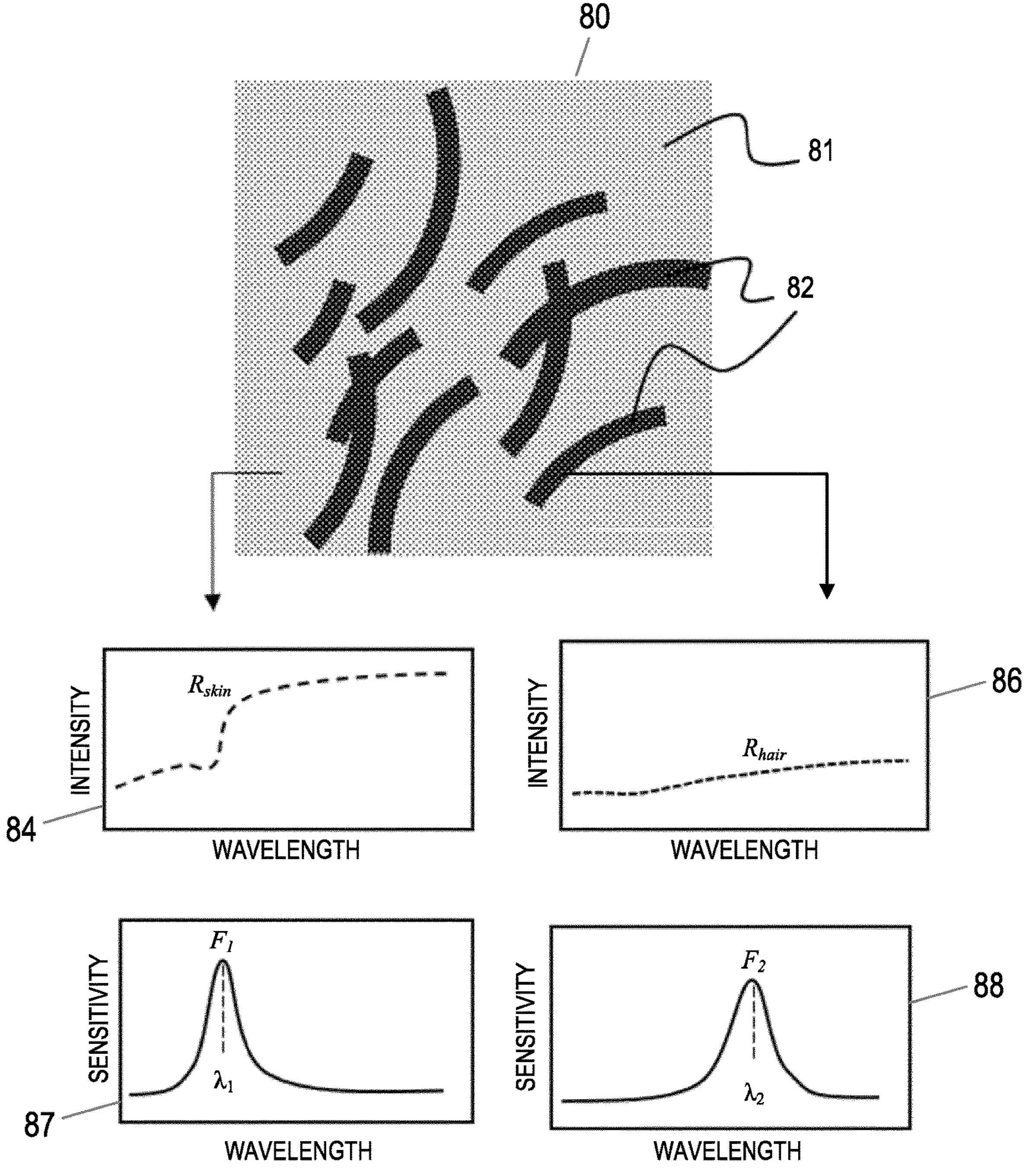
FIG. 8 shows an exemplary image and several graphs/plots illustrating steps of the method in FIG. 7.
Figure 8B:
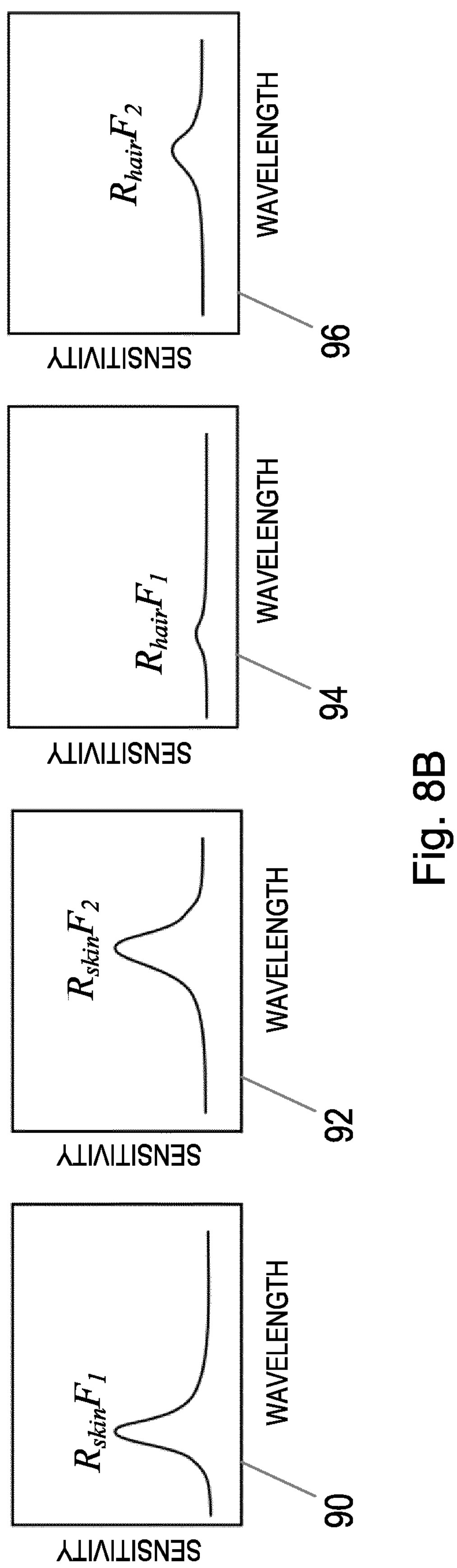

Thus, in step 101, one or more images of a body part of the subject are received by the apparatus 60. The image(s) may have been obtained by an image acquisition unit 64. The image(s) may be received directly from the image acquisition unit 64, for example in real-time as the image(s) are acquired, or the image(s) may be received by retrieving the image(s) from a memory, such as memory unit 68. An exemplary image 80 is shown in FIG. 8. The body part of the subject in the image 80 includes one or more 'skin regions' 81 which are regions of skin on the body part, and one or more 'hair regions' 82 which are regions of hair on the body part. It should be noted that hair regions 82 correspond to the hairs themselves, and the skin region(s) 81 include areas of skin between individual hairs.

In some embodiments, a plurality of images are received in step 101, with each image 80 being obtained for light of a respective wavelength or narrow band of wavelengths. Each image 80 may have been obtained by an image acquisition unit 64 while the body part is sequentially or consecutively illuminated with light of different wavelengths or different narrow bands of wavelengths. Alternatively, the plurality of images can be obtained by an image acquisition unit 64 while the body part is illuminated with white light, and an imaging unit 74 can use a filter or other means to capture a set of images from respective wavelengths of light or from respective different narrow bands of wavelengths.

In step 103, the image(s) 80 are processed to determine the intensity of diffuse reflectance from the skin region(s) 81 at different wavelengths of light. FIG. 8 shows an exemplary graph 84 of the intensity of diffuse reflectance from the skin region(s) 81 for different wavelengths, which is denoted $R_{skin}(\lambda)$. The diffuse reflectance of the skin region(s) 81 for different wavelengths is also referred to as a 'skin region diffuse reflectance spectrum'. Those skilled in the art will appreciate that a diffuse reflectance spectrum is a measurement of the diffuse reflection of light from the sample in the image 80, and excludes the specular reflectance of light from the sample.

In step 105, the image(s) 80 are processed to determine the intensity of diffuse reflectance from the hair region(s) 82 at different wavelengths of light. Step 105 can be performed before, after, or at the same time as, step 103. FIG. 8 shows an exemplary graph 86 of the intensity of diffuse reflectance from the hair region(s) 82 for different wavelengths, which is denoted $R_{hair}(\lambda)$. The diffuse reflectance of the hair region(s) 82 for different wavelengths is also referred to as a 'hair region diffuse reflectance spectrum'.

Step 103 and/or 105 can be performed in a number of different ways. In each case, the intensity of diffuse reflectance at a series of different wavelengths or series of narrow bands of wavelengths reflected from the skin region(s) 81 and reflected from the hair region(s) 82 are determined. In embodiments where each image 80 relates to a specific wavelength or specific narrow band of wavelengths, each image 80 can be analysed to determine the intensity of diffuse reflectance from the skin region(s) 81 and the hair region(s) 82 in the images 80. For an image 80 at a particular wavelength (or narrow band of wavelengths), the intensity of diffuse reflectance from the skin can be determined by averaging the intensity of a number of pixels in the image 80 corresponding to skin region(s) 81. This is repeated for the images 80 at different wavelengths to form the skin region diffuse reflectance spectrum. In some embodiments, only a subset of the pixels corresponding to skin region(s) 81 may be used to determine the intensity of the diffuse reflectance, for example a subset of pixels in a part of the image 80 that does not include and/or is not close to, hair region(s) 82 (e.g. to avoid errors or artefacts due to shadows cast by the hairs, etc.). The hair region diffuse reflectance spectrum can be determined from the images 80 in a similar way.

It will be appreciated that for some of the above embodiments of steps 103 and/or 105, prior to determining the intensity of diffuse reflectance, the received image(s) 80 can be processed in order to identify a part or parts of the image(s) 80 that correspond to skin and a part or parts that correspond to hair. Techniques for identifying skin and/or hair in an image are known in the art, and are not described further herein.

In step 107, a first contrast measure is determined for a first pair of values of first and second wavelengths. In particular the first contrast measure is determined from the diffuse reflectance intensities for the skin region 81 and the hair region 82 in first and second spectral bands of light, with the first and second spectral bands being respectively centred on the value of the first wavelength ($\lambda_1$) and the value of the second wavelength ($\lambda_2$). The first wavelength is a value between 425 nm and 650 nm, and the second wavelength is a value between 600 nm and 850 nm. The spectral bands are also referred to herein as 'detection bands'. Plot 87 in FIG. 8 shows an exemplary first spectral band that is centred on $\lambda_1$, and plot 88 in FIG. 8 shows an exemplary second spectral band that is centred on $\lambda_2$. The first wavelength and the second wavelength have different values. The first spectral band is defined as a function $F_1$ of wavelength $\lambda$ with a peak at $\lambda_1$, and represents a sensitivity curve or filter that is to be applied to the diffuse reflectance spectra determined in steps 103 and 105. Likewise, the second spectral band is defined as a function $F_2$ of wavelength $\lambda$ with a peak at $\lambda_2$, and represents a sensitivity curve or filter that is to be applied to the diffuse reflectance spectra determined in steps 103 and 105.

In some embodiments, a detectable skin diffuse reflectance intensity in the first spectral band, $S_{skin1}(\lambda_1)$, can be determined as:

$$S_{skin1}(\lambda_1) = \sum_{\lambda} R_{skin}(\lambda) F_1(\lambda) \tag{1}$$

i.e. a sum of the product of the first spectral band and the skin region diffuse reflectance spectrum across all wavelengths (or more specifically across 425 nm to 850 nm). The detectable skin diffuse reflectance intensity $S_{skin1}(\lambda_1)$ is shown in plot 90 of FIG. 8.

In these embodiments, a detectable skin diffuse reflectance intensity in the second spectral band, $S_{skin2}(\lambda_2)$, can also be determined as:

$$S_{skin2}(\lambda_2) = \sum_{\lambda} R_{skin}(\lambda) F_2(\lambda) \tag{2}$$

i.e. a sum of the product of the second spectral band and the skin region diffuse reflectance spectrum across all wavelengths (or more specifically across 425 nm to 850 nm). The detectable skin diffuse reflectance intensity $S_{skin2}(\lambda_2)$ is shown in plot 92 of FIG. 8.

In these embodiments, a detectable hair diffuse reflectance intensity in the first spectral band, $S_{hair1}(\lambda_1)$, can also be determined as:

$$S_{hair1}(\lambda_1) = \sum_{\lambda} R_{hair}(\lambda) F_1(\lambda) \tag{3}$$

i.e. a sum of the product of the first spectral band and the hair region diffuse reflectance spectrum across all wavelengths (or more specifically across 425 nm to 850 nm). The detectable hair diffuse reflectance intensity $S_{hair1}(\lambda_1)$ is shown in plot 94 of FIG. 8.

Finally, in these embodiments, a detectable hair diffuse reflectance intensity in the second spectral band, $S_{hair2}(\lambda_2)$, can also be determined as:

$$S_{hair2}(\lambda_2) = \sum_{\lambda} R_{hair}(\lambda) F_2(\lambda) \tag{4}$$

i.e. a sum of the product of the second spectral band and the hair region diffuse reflectance spectrum across all wavelengths (or more specifically across 425 nm to 850 nm). The detectable hair diffuse reflectance intensity $S_{hair2}(\lambda_2)$ is shown in plot 96 of FIG. 8.

In some embodiments, the contrast measure can be determined from a difference between the detected diffuse reflectance intensity for the skin region in the first spectral band (e.g. plot 90) and the detected diffuse reflectance intensity for the skin region in the second spectral band (plot 92), and a difference between the detected diffuse reflectance for the hair region in the first spectral band (plot 94) and the detected diffuse reflectance for the hair region in the second spectral band (plot 96). In some embodiments, the contrast measure is determined from a ratio of these differences. In particular, the contrast measure for the first pair of values of the first and second wavelengths can be determined as:

$$C = \frac{|S_{skin1}(\lambda_1) - S_{skin2}(\lambda_2)|}{|S_{hair1}(\lambda_1) - S_{hair2}(\lambda_2)|} \tag{5}$$

Thus, equation (5) gives the contrast of the skin regions relative to the hair regions. It will be appreciated that (although less preferred) the contrast measure could instead relate to the contrast of the hair regions relative to the skin regions by inverting the ratio in equation (5).

In a computationally more efficient approach than the approach outlined above with regard to equations (1)-(5), having determined the skin region diffuse reflectance spectrum and the hair region diffuse reflectance spectrum in steps 103 and 105, the first contrast measure can be calculated for the first pair of values of the first and second wavelengths directly as:

$$C = \frac{D_{skin}}{D_{hair}} = \frac{\left|\sum_{\lambda} R_{skin}(\lambda) F_1(\lambda) - \sum_{\lambda} R_{skin}(\lambda) F_2(\lambda)\right|}{\left|\sum_{\lambda} R_{hair}(\lambda) F_1(\lambda) - \sum_{\lambda} R_{hair}(\lambda) F_2(\lambda)\right|} \tag{6}$$

As with equation (5), the contrast measure in equation (6) gives the contrast of the skin regions relative to the hair regions.

Next, in step 109, step 107 is repeated for respective further pairs of values of the first and second wavelengths to determine one or more further contrast measures. That is, one or both of the values of the first and second wavelength are changed, and a further contrast measure determined as described above. Step 107 can be repeated any number of times, but preferably contrast measures are determined for a range of values of the first wavelength between 425 nm and 650 nm, and a range of values of the second wavelength between 600 nm and 850 nm.

In some embodiments, a skin spectral difference map can be determined for different values of the first and second wavelengths, and a hair spectral difference map can be determined for different values of the first and second wavelengths. The skin spectral difference map can be given by:

$$D_{skin}(\lambda_1, \lambda_2) = |S_{skin1}(\lambda_1) - S_{skin2}(\lambda_2)| \tag{7}$$

and the hair spectral difference map can be given by:

$$D_{hair}(\lambda_1, \lambda_2) = |S_{hair1}(\lambda_1) - S_{hair2}(\lambda_2)| \tag{8}$$

Finally, in step 111, the plurality of contrast measures are evaluated to select a particular pair of first and second spectral bands. In particular, a pair of first and second spectral bands are selected for which the corresponding pair of values of the first and second wavelengths provide a contrast measure that meets a criterion. For example, the criterion can be the highest contrast measure, and therefore the first and second spectral bands (and the corresponding first and second wavelengths) are selected that provided the highest contrast measure. Mathematically, step 111 can be expressed as:

$$\underset{\lambda_1\lambda_2\Delta\lambda_1\Delta\lambda_2}{\arg\max}\ C, \text{ subject to: } \lambda_1, \lambda_2 \in [425 \text{ nm}, 850 \text{ nm}], \quad \Delta\lambda_1, \Delta\lambda_2 \in [20 \text{ nm}, 200 \text{ nm}] \tag{9}$$

where $\Delta\lambda_1$, $\Delta\lambda_2$ represent the width of the first spectral band and the second spectral band respectively. In some embodiments, the values of $\Delta\lambda_1$, $\Delta\lambda_2$ are fixed, whereas in other embodiments, the width of one or both of the first spectral band and the second spectral band can be varied in repetitions of step 107 to determine different contrast measures. In embodiments where the widths of the first and second spectral bands are not varied, the width of the spectral bands can be set to any value in the range 20 nm to 200 nm.

The criterion evaluated in step 111 can take any suitable form. For example, the criterion could be or include a threshold, and the criterion can be met by a contrast measure that exceeds the threshold. Alternatively, the criterion could be or include a threshold, and the criterion can be met by a contrast measure that is below the threshold. Alternatively, the criterion can be met by the highest of the determined contrast measures. Alternatively, the criterion can be met by the lowest of the determined contrast measures. In another alternative, the criterion is met if the contrast measure is an optimal value. An optimal value is the maximum value, or the minimum value.

In some embodiments, once the first and second spectral bands have been selected in step 111, one or more light sources (e.g. in illumination unit 78) can be used to concurrently or separately illuminate the subject with light including wavelengths corresponding to the selected first and second spectral bands. An imaging unit 74 can be used to obtain one or more further images of the subject while illuminated with this light, and these images received by the processing unit 66. These further images can be analysed to determine one or more properties of the skin and/or hair of the subject.

Alternatively, once the first and second spectral bands have been selected in step 111, the image(s) received in step 101 can be analysed to determine one or more properties of the skin and/or hair of the subject. In particular, where a plurality of images are received in step 101, with each image 80 being obtained for light of a respective wavelength or narrow band of wavelengths, the analysis to determine one or more properties of the skin and/or hair can be performed on the images 80 corresponding to the selected first and second spectral bands.

In either of the above embodiments, the property or properties of hair can include, for example, colour, thickness, shape, density and/or orientation. The property or properties of skin can include, for example, colour, tone, the presence of scars, moles, freckles, spots, etc. Techniques for deriving these properties from images are known in the art, and are not described further herein.

In some embodiments, the results of the analysis can be used in a personal care operation, such as shaving, to improve the performance of the personal care operation and/or to provide feedback to the subject about the personal care operation. For example, the analysis can determine that there are (still) hairs to be shaved on the body part, and therefore the subject needs to shave that part of the body (again) for a cleaner shave, or to achieve a certain facial hair style. On the other hand, the analysis can determine that all hairs have been sufficiently shaved, and the subject can be notified that they don't need to shave that part of the body again, thereby reducing irritation of the skin due to unnecessary shaving strokes. In the case of a personal care operation involving the application of light to the body part, e.g. photoepilation, the results of the analysis of the skin and/or hair can be used to select an appropriate power level for the light output by the photoepilator, and/or an appropriate wavelength of light output by the photoepilator. Any feedback for the subject determined from the analysis of the skin and/or hair can be provided to the subject via the user interface 72. It will be appreciated from the above that to provide guidance and/or feedback on a personal care operation, the image(s) can be obtained, and the analysis of the image(s) performed, during the performance of a personal care operation, e.g. during shaving, or during a photoepilation treatment.

In some embodiments, the method can further comprise receiving or determining an indication of the skin tone of the subject and/or the hair colour of the subject in the image(s) received in step 101. Such an indication can be input by the subject themselves, for example via user interface 72, or the skin tone and/or hair colour can be determined from an analysis of the image(s) themselves as outlined above. The indication of the skin tone and/or hair colour can be stored in a look-up table or database, along with the pair of values of the first and second wavelengths corresponding to the first and second spectral bands selected in step 111.

To expand the look-up table or database, the method in FIG. 7 can be repeated for a number of different subjects with different skin types and/or hair colours, and these skin types and/or hair colours can be stored in the table or database along with an indication of the pair of values of the first and second wavelengths corresponding to the first and second spectral bands selected for the respective subjects.

Thus, when another subject is to be imaged, they can input their skin tone and/or hair colour into the apparatus 60 (e.g. using user interface 72), and the look-up table or database can be consulted to determine the appropriate first and second wavelengths to use for that skin tone and/or hair colour. The illumination unit 78 can be controlled to illuminate the subject with light in the appropriate spectral bands and one or more images of the subject obtained, for analysis to determine other properties of the skin and/or hairs. Alternatively, the subject can be illuminated with white light (e.g. by the illumination unit 78) and appropriate filters can be used by the imaging unit 74 to obtain images from light in the appropriate spectral bands. Again, these images can be analysed to determine other properties of the skin and/or hairs.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method configured for analysing images of hair and skin on a body of a subject, the method comprising:

(i) receiving one or more images of a body part of the subject, the one or more images comprising a skin region corresponding to skin on the body part and a hair region corresponding to hair on the body part;

(ii) processing the one or more images to determine diffuse reflectance of the skin region at different wavelengths of light;

(iii) processing the one or more images to determine diffuse reflectance of the hair region at different wavelengths of light;

(iv) determining a first contrast measure for a first pair of values of first and second wavelengths, wherein the first contrast measure is determined from (a) a difference between the diffuse reflectance intensity for the skin region in the first spectral band and the diffuse reflectance intensity for the skin region in the second spectral band, and (b) a difference between the diffuse reflectance intensity for the hair region in the first spectral band and the diffuse reflectance intensity for the hair region in the second spectral band, wherein the first and second spectral bands are respectively centered on the value of the first wavelength and the value of the second wavelength in the first pair of values;

(v) repeating step (iv) to determine one or more further contrast measures for respective further pairs of values of the first and second wavelengths; and (vi) selecting first and second spectral bands corresponding to the pair of values of the first and second wavelengths that provides a contrast measure that meets a criterion; wherein each value of the first wavelength is in the range between 425 nm and 650 nm, and each value of the second wavelength is in the range between 600 nm and 850 nm, wherein in a pair of values, the value of the first wavelength is different to the value of the second wavelength.

2. A method as claimed in claim 1, wherein step (iv) comprises determining the first contrast measure as a ratio of the differences.

3. A method as claimed in claim 1, wherein one of:

the criterion is met if the magnitude of the contrast measure is above a threshold;

the criterion is met if the magnitude of the contrast measure is below a threshold;

the criterion is met if the contrast measure is the highest of the determined contrast measures;

the criterion is met if the contrast measure is the lowest of the determined contrast measures; and the criterion is met if the contrast measure is an optimal value, wherein the optimal value is the maximum value, or the minimum value.

4. A method as claimed in claim 1, wherein the method further comprises:

controlling one or more light sources to concurrently or separately illuminate the subject with light including wavelengths corresponding to the selected first and second spectral bands; and receiving one or more further images of the subject while the subject is illuminated with the light including wavelengths corresponding to the selected first and second spectral bands.

5. A method as claimed in claim 4, wherein the method further comprises:

analysing the received one or more further images to determine one or more properties of the skin and/or hair of the subject.

6. A method as claimed in claim 1, wherein the method further comprises:

analysing the received one or more images in the selected first and second spectral bands to determine one or more properties of the skin and/or hair of the subject.

7. A method as claimed in claim 1, wherein the method further comprises:

receiving or determining an indication of the skin tone of the subject and/or the hair colour of the subject in the received one or more images.

8. A method as claimed in claim 7, wherein the method further comprises:

repeating the method on images of hair and skin for a plurality of different subjects having different skin tones and/or different hair colours.

9. A method as claimed in claim 7, wherein the method further comprises:

storing, in a look-up table or database, an indication of the selected first and second spectral bands, and/or an indication of the pair of values of the first and second wavelengths corresponding to the selected first and second spectral bands, and the corresponding indication of the tone of the skin and/or colour of the hair.

10. A method as claimed in claim 9, wherein the method further comprises:

receiving an indication of a skin tone and/or a hair colour of a further subject to be imaged; and using the look-up table or database to determine first and second spectral bands to use for imaging the further subject according to the skin tone and/or hair colour in the received indication.

11. A method as claimed in claim 10, wherein the method further comprises:

controlling one or more light sources to illuminate the further subject with light including wavelengths corresponding to the determined first and second spectral bands; and obtaining an image of the further subject while the subject is illuminated with the light including wavelengths corresponding to the determined first and second spectral bands.

12. A method as claimed in claim 11, wherein the method further comprises:

analysing the obtained image of the further subject in the determined first and second spectral bands to determine one or more properties of the skin and/or hair of the further subject.

13. A computer program product comprising a non-transitory computer readable medium having computer readable code embodied therein, the computer readable code being configured such that, on execution by a suitable computer or processor, the computer or processor is caused to perform the method of claim 1.

14. An apparatus configured for analysing images of hair and skin on a body of a subject, the apparatus configured to:

(i) receive one or more images of a body part of the subject, the image comprising a skin region corresponding to skin on the body part and a hair region corresponding to hair on the body part;

(ii) process the one or more images to determine diffuse reflectance of the skin region at different wavelengths of light;

(iii) process the one or more images to determine diffuse reflectance of the hair region at different wavelengths of light;

(iv) determine a first contrast measure for a first pair of values of first and second wavelengths, wherein the first contrast measure is determined (a) a difference between the diffuse reflectance intensity for the skin region in the first spectral band and the diffuse reflectance intensity for the skin region in the second spectral band, and (b) a difference between the diffuse reflectance intensity for the hair region in the first spectral band and the diffuse reflectance intensity for the hair region in the second spectral band, wherein the first and second spectral bands are respectively centered on the value of the first wavelength and the value of the second wavelength in the first pair of values;

(v) repeat operation (iv) to determine one or more further contrast measures for respective further pairs of values of the first and second wavelengths; and (vi) select first and second spectral bands corresponding to the pair of values of the first and second wavelengths that provides a contrast measure that meets a criterion;

wherein each value of the first wavelength is in the range between 425 nm and 650 nm, and each value of the second wavelength is in the range between 600 nm and 850 nm, wherein in a pair of values, the value of the first wavelength is different to the value of the second wavelength.

* * * * *